(12) United States Patent
Stemmer

(10) Patent No.: US 7,560,622 B2
(45) Date of Patent: Jul. 14, 2009

(54) METHODS AND COMPOSITIONS RELATING TO THE GENERATION OF PARTIALLY TRANSGENIC ORGANISMS

(75) Inventor: Willem P. C. Stemmer, Los Gatos, CA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 1341 days.

(21) Appl. No.: 09/970,004

(22) Filed: Oct. 1, 2001

(65) Prior Publication Data

US 2002/0078476 A1    Jun. 20, 2002

Related U.S. Application Data

(60) Provisional application No. 60/238,733, filed on Oct. 6, 2000.

(51) Int. Cl.
C12N 15/31 (2006.01)
C12N 15/52 (2006.01)
C12N 15/82 (2006.01)

(52) U.S. Cl. .................. 800/320.1; 800/288; 800/298; 435/320.1; 536/23.1; 536/24.1

(58) Field of Classification Search ............... 536/23.1, 536/24.1; 435/320.1, 419; 800/295, 278, 800/298, 320, 320.1

See application file for complete search history.

(56) References Cited

U.S. PATENT DOCUMENTS

| | | | |
|---|---|---|---|
| 5,013,659 A | 5/1991 | Bedbrook et al. | |
| 5,670,349 A * | 9/1997 | Cramer et al. | 435/69.1 |
| 5,677,177 A | 10/1997 | Wahl et al. | |
| 5,801,030 A | 9/1998 | McVey et al. | |
| 5,965,791 A * | 10/1999 | Ebinuma et al. | 800/278 |
| 6,010,884 A | 1/2000 | Griffiths et al. | |
| 6,171,861 B1 | 1/2001 | Hartley et al. | |
| 6,187,994 B1 | 2/2001 | Baszczynski et al. | |
| 6,262,341 B1 | 7/2001 | Baszczynski et al. | |
| 6,300,545 B1 | 10/2001 | Baszczynski et al. | |
| 6,331,661 B1 | 12/2001 | Baszczynski et al. | |
| 6,455,315 B1 | 9/2002 | Baszczynski et al. | |
| 6,458,594 B1 | 10/2002 | Baszczynski et al. | |
| 6,541,231 B1 | 4/2003 | Baszczynski et al. | |
| 6,552,248 B1 | 4/2003 | Baszczynski et al. | |
| 6,573,425 B1 | 6/2003 | Baszczynski et al. | |
| 6,624,297 B1 | 9/2003 | Baszczynski et al. | |
| 2002/0124280 A1 | 9/2002 | Li et al. | |
| 2003/0119166 A1 | 6/2003 | Baszczynski et al. | |

FOREIGN PATENT DOCUMENTS

| | | |
|---|---|---|
| WO | WO 92/15694 | 9/1992 |
| WO | WO 92/17484 | 10/1992 |
| WO | WO 93/01283 | 1/1993 |
| WO | WO 93/01283 A1 | 1/1993 |
| WO | WO 93/17116 | 9/1993 |
| WO | WO 94/17176 | 8/1994 |
| WO | WO 95/00555 | 1/1995 |
| WO | WO 95/15972 | 6/1995 |
| WO | WO 96/04393 | 2/1996 |
| WO | WO 97/04103 | 2/1997 |
| WO | WO 97/09436 | 3/1997 |
| WO | WO 97/09439 | 3/1997 |
| WO | WO 97/09439 A1 | 3/1997 |
| WO | WO 97/13401 | 4/1997 |
| WO | WO 97/37012 | * 10/1997 |
| WO | WO 97/37012 A1 | 10/1997 |
| WO | WO 97/47758 | 12/1997 |
| WO | WO 97/48714 | 12/1997 |
| WO | WO 98/54330 | 12/1998 |
| WO | WO 99/07865 | 2/1999 |
| WO | WO 99/11807 | 3/1999 |
| WO | WO 99/23202 | 5/1999 |
| WO | WO 99/25853 | 5/1999 |
| WO | WO 99/55851 | 11/1999 |
| WO | WO 00/17365 A2 | 3/2000 |
| WO | WO 01/36595 A2 | 5/2001 |
| WO | WO 01/36595 A3 | 5/2001 |
| WO | WO 01/40492 A2 | 6/2001 |

OTHER PUBLICATIONS

Gatz, C. (Annu. Rev. Plant Physiol Plant Mol Bio, 1997, vol. 48, 89-108).*
Kononowicz et. al., Plant Cell, vol. 4, No. 5, 1992, pp. 513-524.*
Busk et al. The Plant Journal vol. 11 Issue 6 p. 1285-1295, Jun. 1997.*
Keenan, Robert J., et al., "Non transgenic crops from transgenic plants", *Nature Biotechnology*, (Mar. 2002) 20: pp. 21-22.

(Continued)

*Primary Examiner*—Russell Kallis
(74) *Attorney, Agent, or Firm*—Alston & Bird LLP

(57) ABSTRACT

The present invention provides methods of producing non-transgenic tissues or other agricultural products from a transgenic plant or other transgenic organism. Non-trausgenic organism parts, for example, are derived from transgenic organisms by expression of sequence-specific DNA cleaving enzymes that excise recombinant polynucleotide constructs from the organism's genome by cleaving the constructs at specific recognition sequences that flank the constructs.

31 Claims, 2 Drawing Sheets

OTHER PUBLICATIONS

Russell, Sandra H., et al., "Directed excision of a transgene from the plant genome", *Mol Genet Genet*, (1992) 234: pp. 49-59.

Sugita, Koichi, et al., "A tranformation vector for the production of marker-free transgenic plants containing a single copy transgene at high frequency", *The Plant Journal*, (2000) 22:5, pp. 461-469.

Zubko, Elena, et al., Intrachromoxomal recombination between attP regions as a tool to remove selectable marker genes from tobacco transgenes, *Nature Biotechnology*, (Apr. 2000) 18: pp. 442-444.

Zuo, Jianru, et al., "Chemical-regulated site specific DNA excision in transgenic plants", *Nature Publishing Group*, (Feb. 2001) pp. 157-161.

Sugita, K. et al. "A transformation vector for the production of marker-free transgenic plants containing a single copy transgene at high frequency," *The Plant Journal*, 22(5):461-469 (2000).

Zubko, E. et al. "Intrachromosomal recombination between attP regions as a tool to remove selectable marker genes from tobacco transgenes," *Nature Biotechnology*, vol. 18: 442-445 (2000).

Russell, S.H. et al. "Directed excision of a transgene from the plant genome," *Mol Genet Genet* 234:49-59 (1992).

Zuo, J. et al. "Chemical-regulated, site-specific DNA excision in transgenic plants," *Nature Biotechnology*, vol. 19, No. 2, pp. 157-161 (Feb. 2001).

Keenan, R.J. et al. "Nontransgenic crops from transgenic plants," *Nature Biotechnology*, vol. 20:215-216 (Mar. 2002).

Abremski, K.E., and R. Hoess, "Evidence for a Second Conserved Arginine Residue in the Integrase Family of Recombination Proteins," *Protein Engineering*, 1992, pp. 87-91, vol. 5(1), Oxford University Press.

Albert, H., et al., "Site-Specific Integration of DNA into Wild-Type and Mutant Lox Sites Placed in the Plant Genome," *The Plant Journal*, 1995, pp. 649-659, vol. 7 (4), Plant Gene Expression Center, USDA/ARS-UC Berkeley, Albany, CA.

Araki et al., "Targeted Integration of DNA Using Mutant *Lox* Sites in Embryonic Stem Cells," *Nuc. Acids Res.*, 1997, pp. 868-872, vol. 25(4), Oxford University Press.

Bethke et al., "Segmental Genomic Replacement by Cre-Mediated Recombination: Genotoxic Stress Activation of the p53 Promoter in Single-Copy Transformants," *Nuc. Acids Res.*, 1997, pp. 2828-2834, vol. 25(14), National Institutes of Health, National Institute of Diabetes, Digestive and Kidney Disease, Bethesda, Maryland.

Campbell, W.H., and G. Gowri, "Condon Usage in Higher Plants, Green Algae, and Cyanobacteria," *Plant Physiol.*, 1990, pp. 1-11, vol. 92.

Chiu, W. et al., "Engineered GFP as a Vital Reporter in Plants," *Current Biol.* 1996, pp. 325-330, vol. 6.

Czakó, M., et al., "Negative Selection Markers for Plants," *Technology Transfer of Plant Biotechnology*, 1997, pp. 67-93, Chapter 6, CRC Press, Knoxville, Tennessee.

Dale, E., et al., "Gene Transfer with Subsequent Removal of the Selection Gene From the Host Genome," *Proc. Natl. Acad. Sci. USA*, 1991, pp. 10558-10562, vol. 88, Plant Gene Expression Center, U.S. Department of Agriculture, Berkeley, California.

Dasgupta, I., et al., "Rice Tungro Bacilliform Virus DNA Independently Infects Rice After *Agrobacterium*-Mediated Transfer," *Journal of General Virology*, 1991, pp. 1215-1221, vol. 72.

Esposito, M.S., et al., "Recombinators, Recombinases and Recombination Genes of Yeasts," *Curr. Genetics*, 1994, pp. 1-11, vol. 25.

Feil, R., et al., "Regulation of Cre Recombinase Activity by Mutated Estrogen Receptor Ligand-Binding Domains," *Biochem. Biophys. Res. Commun.*, 1997, pp. 752-757, vol. 237, Academic Press.

Fry, J., et al., "Transformation of *Brassica napus* with *Agrobacterium tumefaciens* Based Vectors," *Plant Cell Rep.*, 1987, pp. 321-325, vol. 6.

Golic, M.M., et al., "FLP-Mediated DNA Mobilization to Specific Target Sites in *Drosophila* Chromosomes," *Nuc. Acids Res.*, 1997, pp. 3665-3671, vol. 25(18), Oxford University Press.

Grimsley, N.H., et al., "Meristematic Tissues of Maize Plants are Most Susceptible to Agroinfection with Maize Streak Virus," *Bio/Technology*, 1988, pp. 185-189, vol. 6.

Karreman, S., et al., "On the Use of Double FLP Recognition Targets (FRTs) in the LTR of Retroviruses for the Construction of High Producer Cell Lines," *Nucleic Acids Research*, 1996, pp. 1616-1624, vol. 24(9).

Kilby et al., "FLP Recombinase in Transgenic Plants: Constitutive Activity in Stably Transformed Tobacco and Generation of Marked Cell Clones in *Arabidopsis*," *Plant J.*, 1995, pp. 637-652, vol. 8(5), University of Cambridge, Cambridge, UK.

Kmiec, E.B., et al., "Genetic Manipulation in Mammalian Cells Using an RNA/DNA Chimeric Oligonucleotide," *Advanced Drug Deliveries Review*, 1995, pp. 333-340, vol. 17.

Lewin, *Gene*, 1983, p. 677.

Lloyd, A.M. and R.W. Davis, "Functional Expression of the Yeast FLP/FRT Site-Specific Recombination System in *Nicotiana tabacum*," *Mol. Gen. Genet.*, 1994, pp. 653-657, vol. 242.

Logie, C., et al., "Ligand-Regulated Site-Specific Recombination," *Proc. Natl. Acad. Sci. USA*, 1995, pp. 5940-5944, vol. 92, European Molecular Biology Laboratory, Heidelberg, Germany.

Louie, R., "Vascular Puncture of Maize Kernels for the Mechanical Transmission of Maize White Line Mosaic Virus and Other Viruses of Maize," *Phytopathology*, pp. 139-143, vol. 85(2), 1995.

Lyznik, L.A., et al., "Activity of Yeast FLP Recombinase in Maize and Rice Protoplasts," *Nuc. Acids Res.*, 1993, pp. 969-975, vol. 21(4), Oxford University Press.

Lyznik, L.A., et al., "FLP-Mediated Recombination of FRT Sites in the Maize Genome," *Nuc. Acids Res.*, 1996, pp. 3784-3789, vol. 24(19), Oxford University Press.

Lyznik, L.A., et al., "Heat-Inducible Expression of FLP Gene in Maize Cells," *Plant J.*, 1995, pp. 177-186, vol. 8(2), Purdue University, West Lafayette, IN.

McLeod, M., et al., "Identification of the Crossover Site During FLP-Mediated Recombination in the *Saccharomyces cerevisiae* Plasmid 2 μm Circle," *Mol. Cell. Biol.*, 1986, pp. 3357-3367, vol. 6(10), American Society for Microbiology, Cold Spring Harbor, New York.

Murray, E.E., et al., "Codon Usage in Plant Cells," *Nucleic Acid Research*, 1989, pp. 477-490.

Narasimhulu, S.B., et al., "Early Transcription of Agrobacterium T-DNA Genes in Tobacco and Maize," *The Plant Cell*, May 1996, pp. 873-886, vol. 8, American Society of Plant Physiologists.

O'Gorman, S. et al., "Protamine-Cre Recombinase Transgenes Efficiently Recombine Target Sequences in the Male Germ Line of Mice, but Not in Embryonic Stem Cells," *Proc. Natl. Acad. Sci. USA*, 1997, pp. 14602-14607, vol. 94, Salk Institute for Biological Studies, San Diego, California.

O'Gorman, S., et al., "Recombinase-Mediated Gene Activation and Site-Specific Integration in Mammalian Cells," *Science*, 1991, pp. 1351-1355, vol. 251, Salk Institute for Biological Studies, La Jolla, California.

Osborne, B., et al., "A System for Insertional Mutagenesis and Chromosomal Rearrangement Using the Ds Transposon and Cre-*lox*," *The Plant Journal*, 1995, pp. 687-701, vol. 7(4).

Ow, D.W., et al., "Genome Manipulation Through Site-Specific Recombination," *Critical Reviews in Plant Sciences*, 1995, pp. 239-261, vol. 14(3).

Raineri, D.M., et al., "VirA, The Plant-Signal Receptor, is Responsible for the Ti Plasmid-specific Transfer of DNA to Maize by Agrobacterium," *Proc. Natl. Acad. Sci.*, 1993, pp. 3549-3553, vol. 90.

Russell, S.H., et al., "Directed Excision of a Transgene from the Plant Genome," *Mol. Genet. Genet.*, 1992, pp. 49-59, vol. 234, MGG Springer-Verlag.

Sadowski, P.D., et al., "Site Specific Genetic Recombination: Hops, Flips, and Flops," *FASEB*, 1993, pp. 760-767, vol. 7.

Sauer, B., "Identification of Cryptic *lox* Sites in the Yeast Genome by Selection for Cre-Mediated Chromosome Translocations that Confer Multiple Drug Resistance," *J. Mol. Biol.*, 1992, pp. 911-928, vol. 223, Academic Press, Ltd., USA.

Sauer, B., "Site-Specific Recombination: Developments and Applications," *Current Opinion in Biotechnology*, 1994, pp. 521-527, vol. 5.

Schlake, T., et al., "Use of Mutated FLP Recognition Target (FRT) Sites for the Exchange of Expression Cassettes at Defined Chromosomal Loci," *Biochem.*, 1994, pp. 12746-12751, vol. 33(43), American Chemical Society.

Scholthof, H.B., et al., "Plant Virus Gene Vectors For Transient Expression of Foreign Proteins in Plants," *Annu. Rev. of Phytopathol.*, 1996, pp. 299-323, vol. 34.

Seibler, J., and J. Bode, "Double-Reciprocal Crossover Mediated by FLP-Recombinase: A Concept and an Assay," *Biochemistry*, 1997, pp. 1740-1747, vol. 36(7).

Senecoff, J.F., et al., "DNA Recognition By The FLP Recombinase of the Yeast 2μ Plasmid: A Mutational Analysis of the FLP Binding Site," *J. Mol. Biol.* 1988, pp. 406-421, vol. 201.

Senecoff, J.F. et al., "Directionality in FLP Protein-Promoted Site-Specific Recombination Is Mediated by DNA-DNA Pairing," *J. Biol. Chem.*, 1986, pp. 7380-7386, vol. 261(16), The American Society of Biological Chemists, Inc., Madison, Wisconsin.

Snaith, M.R., et al., "Multiple Cloning Sites Carrying *loxP* and *FRT* Recognition Sites for the Cre and Flp Site-Specific Recombinases," *Gene*, 1995, pp. 173-174, vol. 166.

Storici, F., et al., "Molecular Engineering with FRT Sequence of the Yeast 2 μm Plasmid: [cir$^o$] Segregant Enrichment By Counterselection for 2 μm Site-Specific Recombination," *Gene*, 1997, pp. 245-255, vol. 195.

Timmermans, M., et al., "Trans Replication and High Copy Numbers of Wheat Dwarf Virus Vectors in Maize Cells," *Nucleic Acids Research*, 1992 pp. 4047-4054, vol. 20(15).

Ugaki, M., et al., "Replication of a Geminivirus Derived Shuttle Vector in Maize Endosperm Cells," *Nucleic Acids Research*, 1991, pp. 371-377, vol. 19(2).

Umlauf, S.W., et al., "The Functional Significance of DNA Sequence Structure in a Site-Specific Genetic Recombination Reaction," 1988, pp. 1845-1852, IRL Press Limited, Oxford, England.

Yoon et al., "Targeted Gene Correction of Episomal DNA in Mammalian Cells Mediated by a Chimeric RNA-DNA Oligonucleotide," *Proc. Natl. Acad. Sci. USA*, pp. 2071-2076, vol. 93, 1996.

Zhang, Y., et al., "Inducible Site-Directed Recombination in Mouse Embryonic Stem Cells," *Nuc. Acids Res.*, 1996, pp. 543-548, vol. 24(4), Oxford University Press.

\* cited by examiner

METHODS AND COMPOSITIONS RELATING TO THE GENERATION OF PARTIALLY TRANSGENIC ORGANISMS

CROSS-REFERENCE TO RELATED PATENT APPLICATIONS

The present invention claims priority from U.S. Provisional Patent Application No. 60/238,733, filed on Oct. 6, 2000, which is incorporated by reference.

FIELD OF THE INVENTION

The present invention pertains to the field of molecular biology. In particular, the invention pertains to the generation of partially transgenic organisms.

BACKGROUND OF THE INVENTION

Recent debates regarding the potential dangers of generation, propagation and consumption of genetically-modified organisms (GMOs) have led to a perception among some consumers that GMOs, and the food products derived from them, are in some way dangerous or unhealthy. For example, recent restrictions on the import of GM foods into Europe have withdrawn an important market from farmers raising genetically modified food crops and animals. Thus, in spite of the agronomically superior traits of some GMOs, farmers may choose to raise non-transgenic plants and animals rather than risk a drop in demand for genetically-modified (GM) foods.

Transformation of organisms typically involves the introduction of a gene of interest (i.e. a "payload" gene) and a selectable marker into the organism. The selectable marker gene is useful in the transformation process to select for, and identify, transformant organisms, but typically provides no useful function once the transformed organism has been identified. In contrast, the goal of transformation technology is to introduce and maintain the payload gene into an organism. PCT Application No. WO 97/37012 describes a system for removing selectable marker genes in transgenic plants by flanking the selectable marker gene with recombination sequences. Following expression of a recombinase, the selectable marker gene is excised, thereby providing a transgenic plant with the associated gene of interest but lacking the selectable marker.

In light of the issues raised by GMOs, there is a need for methods of producing organisms with the advantages of genetic engineering that produce non-transgenic products. The invention presented herein addresses this and other problems.

SUMMARY OF THE INVENTION

The invention provides methods of creating a transgenic plant capable of producing a non-transgenic agricultural product. In general, the methods of the invention comprise introducing into a plant a polynucleotide excision construct flanked by a first pair of recognition sequences. The excision construct comprises a first expression cassette comprising a non-constitutive first excision promoter operably linked to a polynucleotide encoding a first sequence-specific DNA cleaving enzyme. The excision construct also comprises a second expression cassette comprising a promoter operably linked to a payload polynucleotide conferring one or more agronomically important trait on the plant. The methods of the invention further comprise expressing the first sequence-specific DNA cleaving enzyme, thereby cleaving the recognition sequences and excising the excision construct from at least part of the transgenic plant.

The invention also provides for nucleic acids comprising a polynucleotide excision construct flanked by a first pair of recognition sequences, the construct comprising (1) a first expression cassette comprising a first excision promoter operably linked to a polynucleotide encoding a first sequence-specific DNA cleaving enzyme, wherein the first excision promoter is not constitutive; and (2) a second expression cassette comprising a promoter operably linked to a polynucleotide conferring an agronomically important trait on the plant.

The invention also provides for a plant comprising a polynucleotide excision construct flanked by a first pair of recognition sequences, the construct comprising (1) a first expression cassette comprising a first excision promoter operably linked to a polynucleotide encoding a first sequence-specific DNA cleaving enzyme, wherein the first excision promoter is not constitutive; and (2) a second expression cassette comprising a promoter operably linked to a polynucleotide conferring an agronomically important trait on the plant. In some embodiments, at least one cell of the plant is free of the excision construct.

In some embodiments, the polynucleotide is excised from the entire transgenic plant.

The first excision promoter can be inducible. For instance, the promoter can be chemically inducible. In some of these embodiments a tissue-specific promoter can be oriented at the far end of the polynucleotide encoding the sequence-specific DNA cleaving enzyme such that expression of the enzyme is prevented in the tissues where the tissue-specific promoter is active.

Alternatively, the first excision promoter can be tissue-specific, e.g., a fruit specific promoter or a seed-specific promoter. In some embodiments, the first excision promoter is induced under low moisture conditions.

In some embodiments, the polynucleotide excision construct comprises a polynucleotide for maintenance of the construct in the seed, wherein the polynucleotide is capable of preventing expression of the first sequence-specific DNA cleaving enzyme. For example, the polynucleotide excision construct can comprise a second pair of recognition sequences disrupting the first excision promoter, and an inducible second excision promoter operably linked to a polynucleotide encoding a second sequence-specific DNA cleaving enzyme capable of cleaving the second pair of recognition sequences. For example, in some of these embodiments, the second pair of recognition sequences flank the second inducible promoter operably linked to a polynucleotide encoding a second sequence-specific DNA cleaving enzyme.

In some embodiments, the polynucleotide excision construct comprises an inducible promoter operably linked to a polynucleotide encoding a repressor capable of repressing expression from the first excision promoter. In some embodiments, the polynucleotide encoding the sequence-specific DNA cleaving enzyme is flanked by an inducible second excision promoter oriented such that induction prevents expression of the first sequence-specific DNA cleaving enzyme. Alternatively, the polynucleotide excision construct can comprise an inducible second excision promoter operably linked to a sense or antisense polynucleotide capable of preventing expression of the first sequence-specific DNA cleaving enzyme.

In some embodiments, the first sequence-specific DNA cleaving enzyme cleaves within the recognition sequence. For example, the first sequence-specific DNA cleaving enzyme can be a recombinase, resolvase, restriction enzyme or transposase. In some embodiments, the recombinase is Cre and the recognition sequence is a lox sequence.

In some embodiments, the the first sequence-specific DNA cleaving enzyme cleaves outside the recognition sequence, thereby excising all non-native sequences associated with the polynucleotide construct. For example, the sequence-specific DNA cleaving enzyme can be a class IIs Restriction/Modification (R-M) enzyme.

Definitions

"Non-transgenic agricultural product" refers to any cell, tissue, or other product of a GMO (e.g., a transgenic plant, animal or microorganism) that is free of transgene DNA as defined here. As used herein, a cell is free of transgene DNA even if the cell comprises a DNA footprint (i.e. a short non-coding DNA sequence) resulting from the excision of a genetic construct according to the methods of the invention.

"Recognition sequence" refers to a DNA sequence that is recognized by a sequence-specific DNA cleaving enzyme of the invention. The recognition sequence will typically be at least two base pairs long, is more usually 6 to 30 base pairs long, and in most embodiments, is less than 50 base pairs long. Examples of recognition sequences include sequences recognized by recombinases (e.g., lox sites), resolvases, transposases and restriction enzymes.

A "sequence-specific DNA cleaving enzyme" refers to a polypeptide capable of catalyzing the cleavage or recombination of a DNA molecule at one or more recognition sequences. Examples of sequence-specific DNA cleaving enzymes include recombinases (e.g., Cre), resolvases, integrases, transposases, restriction enzymes, and the like.

"Agronomically important traits" include any phenotype in an organism that is useful or advantageous for food production or food products, including plant parts, plant products, and animal and microorganism (e.g., yogurt) products. Non-food agricultural products such as paper, etc. are also included. A partial list of agronomically important traits includes pest resistance, vigor, development time (time to harvest), enhanced nutrient content, novel growth patterns, flavors or colors, salt, heat, drought and cold tolerance, and the like. Agronomically important traits do not include selectable marker genes (e.g., genes encoding herbicide or antibiotic resistance used only to facilitate detection or selection of transformed cells), hormone biosynthesis genes leading to the production of a plant hormone (e.g., auxins, gibberllins, cytokinins, abscisic acid and ethylene that are used only for selection), or reporter genes (e.g. luciferase, β-glucuronidase, chloramphenicol acetyl transferase (CAT, etc.).

"Part of a GMO" refers to any tissue or cell of an organism, so long as the whole organism is not included. Thus, a "part of a plant" refers to any tissue or cell of a plant, so long as the whole plant is not included.

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

A "polynucleotide construct" refers to a nucleic acid at least partly created by recombinant methods.

The term "promoter" refers to regions or sequence located upstream and/or downstream from the start of transcription and which are involved in recognition and binding of RNA polymerase and other proteins to initiate transcription. The term "excision promoter" refers to a promoter operably linked to a polynucleotide encoding a sequence-specific DNA cleaving enzyme.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety).

"Transgene" or "recombinant" refers to an exogenous human manipulated polynucleotide or a copy or complement of a human manipulated polynucleotide. For instance, a transgene expression cassette comprising a promoter operably linked to a second polynucleotide may include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)) of an isolated nucleic acid comprising the expression cassette. In another example, a recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

A polynucleotide "exogenous to" an individual organism is a polynucleotide which is introduced into the organism by any means other than by a sexual cross.

A "genetically-modified organism" or "GMO" refers to any organism that comprises transgene DNA. Exemplary organisms include plants, animals and microorganisms.

DESCRIPTION OF THE SPECIFIC EMBODIMENTS

The present invention provides methods of producing non-transgenic tissues or other products from a GMO, such as a transgenic plant, animal or microorganism. The invention provides, for instance, a polynucleotide "excision" construct comprising a first expression cassette comprising an excision cassette comprising an excision promoter operably linked to a polynucleotide encoding a sequence-specific DNA cleaving enzyme and a second expression cassette comprising a promoter operably linked to a "payload" polynucleotide, i.e., a gene of interest. The excision construct is flanked by recognition sequences. The payload polynucleotide can comprise, for example, a polynucleotide conferring an agronomically-important trait. The polynucleotide construct may optionally also comprise a selectable marker gene.

Figure 1:
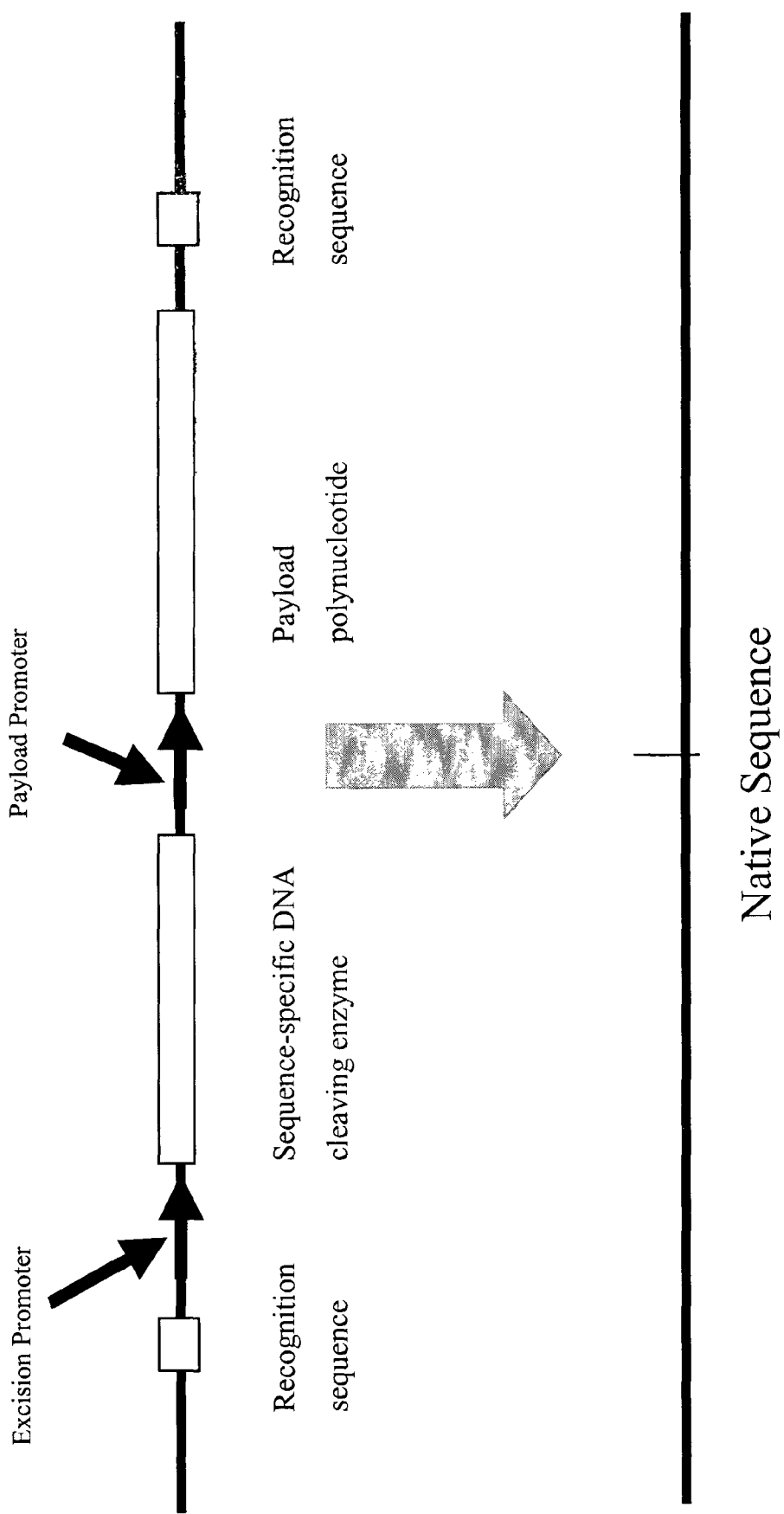
FIG. 1 is a schematic representation of a polynucleotide construct of the invention before and after the sequence-specific DNA cleaving enzyme is expressed. Horizontal arrows indicate promoters.

Non-transgenic organism parts, such as specific tissues, organs or cell types, are derived from GMOs by expression of the sequence-specific DNA cleaving enzyme, which excises the polynucleotide excision construct from the GMO genome by cleaving at the specific recognition sequences that flank the construct. Expression of the sequence-specific DNA cleaving enzyme is controlled by the excision promoter (FIG. 1). For example, the first excision promoter directs expression of the sequence-specific DNA cleaving enzyme when so desired in a particular cell type(s) or tissue(s). For instance, the first excision promoter can be tissue-specific or can be induced at a stage or in a tissue of cell-type of an organism when non-transgenic organism tissues or cell types are desired. Therefore, only those tissues where the excision promoter is expressed will lack the polynucleotide construct. In some embodiments, multiple copies of the same payload gene are operably linked to different excision promoters.

In some circumstances, recombinant constructs of the GMO can be excised from the reproductive organs of the organism. For example, fruit and seed is a major commercial product to which the methods of the invention can be applied. It is useful, however, to have a system to maintain the excision construct of the invention in the organism. For example, it is useful to propagate organisms containing the transgenes of the invention. The invention provides genetic constructs and methods of maintaining the recombinant constructs of the invention in any tissue, including reproductive tissue, for propagation of new transgenic organisms.

The compositions and methods of the invention can be illustrated by reference to production of transgenic plants. One of skill in the art will recognize, however, that the same or similar embodiments can be applied to other organisms such as animals and microorganisms.

I. Sequence-Specific DNA Cleaving Enzymes

The methods of the invention employ a sequence-specific DNA cleaving enzyme to excise the polynucleotide excision constructs of the invention from a transgenic organism. Preferably, the sequence-specific DNA cleaving enzyme is capable of cleaving a recognition sequence such that all, or substantially all, transgenic DNA is removed from the genome of the tissues or cells where the DNA cleaving enzyme is expressed. Depending on the DNA cleaving enzyme, a small DNA "footprint" can be left behind from the cleaving reaction. The footprint is typically created when the DNA cleaving enzyme cleaves in the middle of a recognition sequence, as discussed below.

In some aspects of the invention, the sequence-specific cleaving enzyme can ligate the genomic DNA after cleaving out the transgenic DNA. In these embodiments, the resulting chromosomal DNA is one contiguous polynucleotide. In another aspect, the sequence-specific cleaving enzyme does not ligate the cleaved chromosomal DNA. In these aspects, endogenous cellular ligases can act to religate and/or repair the genomic DNA. Those of skill in the art will recognize that such ligation reactions are particularly efficient if the DNA has been cleaved such that the ends of the DNA have complementary single-stranded overhanging ends.

In presently preferred embodiments, a gene that encodes the sequence-specific DNA cleaving enzyme is introduced into the cells. Expression of the gene results in production of the DNA cleaving enzyme, which then catalyzes a cleavage reaction at the corresponding recognition sequences. One can introduce the DNA cleaving enzyme gene into the cell before, after, or simultaneously with, the introduction of the exogenous polynucleotide of interest. In a preferred embodiment, the DNA cleaving enzyme gene is present within the vector that carries the polynucleotide construct that is to be inserted and is flanked by a pair of recognition sequences (FIG. 1).

Preferably, recognition sequences are rarely, if ever found in the genome of the transgenic organism. Ideally, the only copies of the recognition sequences in the genome flank the construct, thereby eliminating the chance that other DNA in the genome is excised when the sequence-specific DNA cleaving enzyme is expressed.

Depending on the sequence-specific DNA cleaving enzyme, excision of the construct can result from cleavage in or outside of the recognition sequence. If the enzyme cleaves outside of the recognition sequence and away from the excision construct, then no recombinant DNA will be left within the genome of that cell of the transgenic organism. However, if the DNA cleaving enzyme cleaves within the recognition sequence, then a DNA footprint will remain in the genome of the cell. This footprint need not be a "transgene," however, if the excision construct is introduced (e.g., by homologous recombination) into a part of the genome where the footprint sequence already naturally occurs. In this case, excision leaves the exact naturally occurring sequence. In a third aspect, the footprint does not match the native sequence. In this case, excision of the excision construct leaves at least a short non-native sequence. For example, excision from lox sequences catalyzed by Cre (see below) produces about a 30 base pair footprint.

In some aspects of the invention, molecular evolution can be employed to create an improved sequence specific DNA cleaving enzyme that cleaves a recognition sequence at a desired location. For example, a sequence-specific DNA cleaving enzyme that cleaves outside of the outermost nucleotide of the recognition sequence can be selected. Such enzymes are useful for the method of the invention because excision of the excision construct would not leave behind a genetic footprint and would not alter the native genomic sequence.

Additionally, it is possible to select DNA cleaving enzymes with the ability to cleave in specific or randomly selected native DNA sequences. For example a library of enzyme variants can be constructed and then tested for their ability to cleave DNA sequences within a particular polynucleotide sequence. In some aspects, the polynucleotide tested can comprise an entire chromosome or genome. As a result of this method, sequence-specific DNA cleaving enzymes can be selected that cleave a native (i.e., non-recombinant) DNA sequence in an organism. Once such enzymes are identified, they can be further enhanced through subsequent rounds of molecular evolution. Thus, the expression of the enzyme, as well as the activity of the enzyme can be altered relative to the particular DNA sequence that the enzyme recognizes and cleaves.

Polynucleotides encoding a candidate DNA cleaving enzyme can be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer, *Proc. Natl. Acad. Sci. USA* 91:10747-10751 (1994); Stemmer, *Nature* 370:389-391 (1994); and U.S. Pat. Nos. 5,605,793, 5,837,458, 5,830,721 and 5,811,238.

Without limiting the invention, four examples of sequence-specific DNA cleaving enzymes (recombinases, resolvases, integrases, transposases and restriction enzymes) are described below.

Recombinases, Resolvases and Transposases

Recombinases, resolvases and transposases each catalyze the cleavage of DNA at one or more recognition sequences, followed by the subsequent ligation of DNA. These enzymes can be used according to the methods of the invention to catalyze the excision of the excision construct from an organism's genome. The enzymes also catalyze the subsequent ligation of the cleaved genomic DNA ends, thereby returning the organism's genome to a nontransgenic state.

A recombinase catalyzes a recombination reaction between specific recognition sequences. Recombination sites typically have an orientation. In other words, they are not perfect palindromes. In some aspects, the orientation of the recognition sequences in relation to each other determines what recombination event takes place. The recombination sites may be in two different orientations: parallel (same direction) or opposite. When the recombination sites are in an opposite orientation to each other, then the recombination event catalyzed by the recombinase is an inversion. When the recombination sites are in a parallel orientation, then any intervening sequence is excised. The reaction can often leave a single recombination site in the genome following excision. It is this second orientation that is used in the methods of the invention to excise the transgenic construct. The remaining recognition sequences may or may not be altered, depending on the recombination fidelity of the recombinase.

One recombination system is the Cre-lox system. In the Cre-lox system, the recognition sequences are referred to as "lox sites" and the recombinase is referred to as "Cre". When lox sites are in parallel orientation (i.e., in the same direction), then Cre catalyzes a deletion of the intervening polynucleotide sequence. When lox sites are in the opposite orientation, the Cre recombinase catalyzes an inversion of the intervening polynucleotide sequence. This system has been described in various host cells, including *Saccharomyces cerevisiae* (Sauer, B., *Mol Cell Biol.* 7:2087-2096 (1987)); mammalian cells (Sauer, B. et al., *Proc. Natl Acad. Sci. USA* 85:5166-5170 (1988); Sauer, B. et al., *Nucleic Acids Res.* 17:147-161 (1989)); and plants such as tobacco (Dale, E. et al., *Gene* 91:79-85 (1990)) and *Arabidopsis* (Osborne, B. et al., *Plant J.* 7(4):687-701 (1995)). Use of the Cre-lox recombinase system in plants is also described in U.S. Pat. No. 5,527,695 and PCT application No. WO 93/01283. Several different lox sites are known, including lox511 (Hoess R. et al., *Nucleic Acids Res.* 14:2287-2300 (1986)), lox66, lox71, lox76, lox75, lox43, lox44 (Albert H. et al., *Plant J.* 7(4): 649-659 (1995)).

Several other recombination systems are also suitable for use in the invention. These include, for example, the FLP/FRT system of yeast (Lyznik, L. A. et al., *Nucleic Acids Res.* 24(19):3784-9 (1996)), the Gin recombinase of phage Mu (Crisona, N. J. et al., *J. Mol. Biol.* 243(3):437-57 (1994)), the Pin recombinase of *E. coli* (see, e.g., Kutsukake K, et. al., *Gene* 34(2-3):343-50 (1985)), the PinB, PinD and PinF from *Shigella* (Tominaga A et al., *J. Bacteriol.* 173(13):4079-87 (1991)), the R/RS system of the pSR1 plasmid (Araki, H. et al., *J. Mol Biol* 225(1):25-37 (1992)), recombination systems in theta-replicating bacteria (Alonso, et al, *Ann. Rev. Biochem.* 66:437-474 (1997) and the shufflon systems found in some prokaryotes (Komano, *Ann. Rev. Genetics Res. Microbiol.* 150(9-10):641-51 (1999). Other recombination systems include the integrase family of recombinases (Grainge, et al., *Molec. Microbiol.* 33(3):449-56 (1999); Gopaul et al., *Curr. Opin. Struct. Biol.* 9(1):14-20 (1999); Yang, et al., *Structure* 5(11):1401-6 (1997)). Thus, recombinase systems are available from a large and increasing number of sources. Recombinase systems may be employed in the cells of any organism that can be transformed with nucleic acids.

Resolvases and transposases can also be used in the methods of the invention to excise the construct from the genome of an organism. Resolvases act to recombine DNA fragments at specific recognition sequences. See, Hall, et al., *Nucleic Acids Res.* 21:5712-5719 (1993). Resolvases are typically one of two enzymes that are involved in prokaryotic transposon movement. Examples of resolvases include the tn3 resolvase gene, tnp R (Heffron, F., MOBILE GENETIC ELEMENTS (Shapiro, J. A., ed.) New York Academic Press, NY (1983), pp 223-260; and Heffron, F., et al., *Cell* 18:1153-1163 (1979)), the hjc gene product (Kvaratskhelia, et al., *J. Mol. Biol.* 297 (4):923-32 (2000)), RuvC (Garcia, et al., *Proc Natl Acad Sci USA* 97(16):8926-8931 (2000)), rlgA: (Massey, et al., *Plasmid* 44(1):24-33 (2000)), ccrA and ccrB (Katayama, et al., *Antimicrob Agents Chemother* 44(6):1549-55 (2000)) and CCE1 (Fogg, et al., *Biochemistry* 39(14):4082-9 (2000)).

Eukaryotic transposases also have the ability to recombine DNA at specific recombination sequences, thereby excising the intervening DNA. See, Haren L, et al., *Annu Rev Microbiol* 53:245-81 (1999); Hallet B, et al., *FEMS Microbiol Rev.* 21(2):157-78 (1997). Transposases include, e.g., the maize AC transposase (Haring, et al., *Plant Mol Biol* 16(3):449-61 (1991)), *Drosophila* P elements (Lankenau, *Chromosoma* 103(10):659-68 (1995)), insect Tc1/mariner transposons (Plasterk, *Curr. Top. Microbiol. Immunol.* 204:125-43 (1996); Plasterk, et al., *Trends Genet* 15(8):326-32 (1999)), including the fish sleeping beauty transposon (Ivics, *Cell* 91(4):501-10 (1997)) and yeast Ty elements (Kim, *Genome Res* 8(5):464-78 (1998)).

Restriction Enzymes

Restriction enzymes cleave DNA at recognition sequences (commonly known as restriction sequences), thereby releasing the construct from the genome. Unlike recombinases, restriction enzymes typically do not ligate DNA, but only cleave DNA. Restriction enzymes are described, for instance, in the New England Biolabs online catalog (www.neb.com/), Promega online catalog (www.promoega.com/) and Rao, et al. *Prog Nucleic Acid Res Mol Biol* 64:1-63 (2000). Restriction enzymes that recognize recognition sequences that are at least 8 base pairs long are preferred. A restriction enzyme that cleaves a 10 base pair recognition sequence is described in Huang B, et al. *J. Protein Chem.* 15(5):481-9 (1996).

Class IIs R-M restriction enzymes catalyze the DNA cleavage at sequences other than the recognition sequence, i.e. they cleave at a DNA sequence at a particular number of nucleotides away from the recognition sequence (Szybalski, et al., *Gene* 100:13-26 (1991)). Class IIs R-M restriction enzymes are a preferred DNA cleaving enzyme of the invention, because when the recognition sequences are oriented properly, the enzymes delete the entire construct and recognition sequence, thereby leaving the genome completely free of transgenic sequences. Examples of class IIs restriction enzymes include Fok I, Alw26 I, Bbv I, Bsr I, Ear I, Hph I, Mbo II, SfaN I and Tth111.

Other restriction enzymes that cleave rarely in DNA sequences include Alw I, Bbs I, Bbv I, BciVI, Bmr I, Bpm I, Bsa I, BseRI, Bsg I, BsmAI, BsmBI, BsmFI, BspMI, BsrDI, BstnBI, Bts I, Ear I, Eci I, Fau I, Fok I, Hga I, Hph I, Mbo II, Mly I, Mnl I, Ple I, Sap I and Sean I. Restriction enzymes with particularly long recognition sequences, and which therefore only rarely (if ever) cleave within a genome include: I-CeuI (26 bp recognition sequence), PI-PspI (30 bp recognition sequence), PI-Sce-I (39 bp recognition sequence), I-SceI (18 bp recognition sequence) and I-Ppoi (15 bp recognition sequence). The restriction enzymes can generally be obtained from New England Bioloabs, Beverly, Mass., or Promega Corp., Madison, Wis.

II. Promoters of the Invention

In addition to the recognition sequences and a polynucleotide encoding a sequence-specific DNA cleaving enzyme, the polynucleotide excision constructs of the invention comprise an excision promoter, as well as a promoter for expression of the payload polynucleotide, i.e., a gene of interest. Selection of the excision promoter is usually determined by the time or tissue that excision is desired. For example, the excision promoter can be expressed in a specific tissue of the GMO or, alternatively, the promoter can be inducible. Similarly, the payload promoter is selected for what tissues or cells expression of the payload gene is desired.

A number of exemplary promoters are described below. The following promoters, however, are only provided as examples and are not intended to limit the invention. Those of skill in the art will recognize that other promoters with desired expression patterns are well known or can be selected with routine molecular techniques.

A promoter can be derived from a gene that is under investigation, or can be a heterologous promoter that is obtained from a different gene, or from a different species. Where expression of a gene in all tissues of a transgenic plant or other organism is desired, one can use a "constitutive" promoter, which is generally active under most environmental conditions and states of development or cell differentiation. The payload promoter can be constitutive. The excision promoter, however, is not constitutive because the excision promoter promotes expression of the sequence-specific cleaving enzyme in only part of an organism's life cycle or tissue.

Suitable constitutive promoters for use in plants include, for example, the cauliflower mosaic virus (CaMV) 35S transcription initiation region and region VI promoters, the 1'- or 2'-promoter derived from T-DNA of *Agrobacterium tumefaciens*, and other promoters active in plant cells that are known to those of skill in the art. Other suitable promoters include the full-length transcript promoter from Figwort mosaic virus, actin promoters, histone promoters, tubulin promoters, or the mannopine synthase promoter (MAS). Other constitutive plant promoters include various ubiquitin or polyubiquitin promoters derived from, inter alia, *Arabidopsis* (Sun and Callis, *Plant J.*, 11(5):1017-1027 (1997)), the mas, Mac or DoubleMac promoters (described in U.S. Pat. No. 5,106,739 and by Comai et al., *Plant Mol. Biol.* 15:373-381 (1990)) and other transcription initiation regions from various plant genes known to those of skill in the art. Useful promoters for plants also include those obtained from Ti- or Ri-plasmids, from plant cells, plant viruses or other hosts where the promoters are found to be functional in plants. Bacterial promoters that function in plants, and thus are suitable for use in the methods of the invention include the octopine synthetase promoter, the nopaline synthase promoter, and the mannopine synthetase promoter. Suitable endogenous plant promoters include the ribulose-1,6-biphosphate (RUBP) carboxylase small subunit (ssu) promoter, the α-conglycinin promoter, the phaseolin promoter, the ADH promoter, and heat-shock promoters.

Promoters for use in gram positive and gram negative bacteria (e.g., *E. coli*) include the T7, trp, or lambda promoters, a ribosome binding site and preferably a transcription termination signal. For eukaryotic cells, including animal cells, the control sequences typically include a promoter which optionally includes an enhancer derived from immunoglobulin genes, SV40, cytomegalovirus, etc., and a polyadenylation sequence, and may include splice donor and acceptor sequences. In yeast, convenient promoters include GAL1-10 (Johnson and Davies (1984) *Mol. Cell. Biol.* 4:1440-1448) ADH2 (Russell et al. (1983) *J. Biol. Chem.* 258:2674-2682), PHO5 (*EMBO J.* (1982) 6:675-680), and MFα (Herskowitz and Oshima (1982) in THE MOLECULE BIOLOGY OF THE YEAST SACCHAROMYCES (eds. Strathern, Jones, and Broach) Cold Spring Harbor Lab., Cold Spring Harbor, N.Y., pp. 181-209).

Of course, promoters can be expressed all of the time in only one or some tissues. Alternatively, a promoter can be expressed in all tissues but only at a specific developmental time point. As noted above, the excision promoter (i.e., the promoter that is linked to the sequence-specific DNA cleaving polynucleotide) is generally not constitutive, but instead is active for only part of the life cycle or at least one tissue of the transgenic organism. For example, the excision promoter can be a tissue-specific or inducible promoter. One can use a promoter that directs expression of a gene of interest in a specific tissue or is otherwise under more precise environmental or developmental control. Examples of environmental conditions that may effect transcription by inducible promoters include pathogen attack, anaerobic conditions, ethylene or the presence of light. Promoters under developmental control include promoters that initiate transcription only in certain tissues, such as leaves, roots, fruit, seeds, or flowers, or parts thereof. The operation of a promoter may also vary depending on its location in the genome. Thus, an inducible promoter may become fully or partially constitutive in certain locations. Inducible promoters are often used to control expression of the recombinase gene, thus allowing one to control the timing of the recombination reaction. Examples of tissue-specific plant promoters under developmental control include promoters that initiate transcription only in certain tissues, such as fruit, seeds, or flowers. The tissue-specific E8 promoter from tomato is particularly useful for directing gene expression so that a desired gene product is located in fruits. See, e.g., Lincoln et al. (1988) *Proc. Nat'l. Acad. Sci. USA* 84: 2793-2797; Deikman et al. (1988) *EMBO J.* 7: 3315-3320; Deikman et al. (1992) *Plant Physiol.* 100: 2013-2017. Other suitable seed specific promoters include those derived from the following genes: MAC1 from maize (Sheridan et al. *Genetics* 142:1009-1020 (1996), Cat3 from maize (GenBank No. L05934, Abler et al. *Plant Mol. Biol.* 22:10131-1038 (1993), the gene encoding oleosin 18 kD from maize (GenBank No. J05212, Lee et al. *Plant Mol. Biol.* 26:1981-1987 (1994)), viviparous-1 from *Arabidopsis* (Genbank No. U93215), the gene encoding oleosin from *Arabidopsis* (Genbank No. Z17657), Atmyc1 from *Arabidopsis* (Urao et al. *Plant Mol. Biol.* 32:571-576 (1996), the 2s seed storage protein gene family from *Arabidopsis* (Conceicao et al. *Plant* 5:493-505 (1994)) the gene encoding oleosin 20 kD from *Brassica napus* (GenBank No. M63985), napA from *Bras-* sica napus (GenBank No. J02798, Josefsson et al. *JBL* 26:12196-1301 (1987), the napin gene family from *Brassica napus* (Sjodahl et al. *Planta* 197:264-271 (1995), the gene encoding the 2S storage protein from *Brassica napus* (Dasgupta et al. *Gene* 133:301-302 (1993)), the genes encoding oleosin A (Genbank No. U09118) and oleosin B (Genbank No. U09119) from soybean and the gene encoding low molecular weight sulphur rich protein from soybean (Choi et al. *Mol Gen, Genet.* 246:266-268 (1995)).

Examples of environmental conditions that may affect transcription by inducible promoters include anaerobic conditions, elevated temperature, or the presence of light. Inducible promoters typically have a low base-line expression and can be strongly inducible. Additional organ-specific, tissue-specific and/or inducible foreign promoters are also known (see, e.g., references cited in Kuhlemeier et al (1987) *Ann. Rev. Plant Physiol.* 38:221), including those 1,5-ribulose bis-phosphate carboxylase small subunit genes of *Arabidopsis thaliana* (the "ssu" promoter), which are light-inducible and active only in photosynthetic tissue, anther-specific promoters (EP 344029), and seed-specific promoters of, for example, *Arabidopsis thaliana* (Krebbers et al. (1988) *Plant Physiol.* 87:859). Exemplary green tissue-specific promoters include the maize phosphenol pyruvate carboxylase (PEPC) promoter, small subunit ribulose bis-carboxylase promoters (ss-RUBISCO) and the chlorophyll a/b binding protein promoters. The promoter may also be a pith-specific promoter, such as the promoter isolated from a plant TrpA gene as described in International Publication No. WO93/07278.

Inducible promoters for other organisms include, for example, the arabinose promoter, the lacZ promoter, the metallothionein promoter, copper-induced promoter, rbcS promoter and other light induced promoters and the heat shock promoter. Other examples of inducible promoters include tetracycline and other hormone inducible expression systems, and the like. Hormones that have been used to regulate gene expression include, for example, estrogen, tomoxifen, toremifen and ecdysone (Ramkumar and Adler *Endocrinology* 136: 536-542 (1995)). See, also, Gossen and Bujard *Proc. Nat'l. Acad. Sci. USA* 89: 5547 (1992); Gossen et al. *Science* 268:1766 (1995). In tetracycline-inducible systems, tetracycline or doxycycline modulates the binding of a repressor to the promoter, thereby modulating expression from the promoter. An additional example includes the ecdysone responsive element (No et al., *Proc. Nat'l. Acad. Sci. USA* 93:3346 (1997)). Other examples of inducible promoters include the glutathione-S-transferase II promoter which is specifically induced upon treatment with chemical safeners such as N,N-diallyl-2,2-dichloroacetamide (PCT Application Nos. WO 90/08826 and WO 93/01294) and the alcA promoter from *Aspergillus*, which in the presence of the alcR gene product is induced with cyclohexanone (Lockington, et al., *Gene* 33:137-149 (1985); Felenbok, et al. *Gene* 73:385-396 (1988); Gwynne, et al. *Gene* 51:205-216 (1987)) as well as ethanol. Chemical inducers of promoters can be combined with other active chemicals or inert carriers prior to application to an organism. For example, other agronomically useful chemical compositions such as pesticides or fertilizers as well as carriers and solvents can be combined with the inducer.

III. Payload Polynucleotides

Payload polynucleotides are polynucleotide sequences that are introduced into an organism to confer a desired phenotype. One advantage of the present invention is that desired traits can be conferred upon an organism, but the polynucleotides conferring the traits can be excised prior to commercialization of the organism or products from the organism. For example, excision can occur when seed are harvested, upon sale of the seed, during processing or any other time prior to consumption. Thus, any polynucleotide sequences can be introduced into an organism according to the invention. Preferably, the polynucleotides comprise genes conferring agronomically important traits or commercially important traits.

In plants, payload genes include genes that confer agronomically important traits such as pest resistance (e.g., Melchers, et al., *Curr Opin Plant Biol.* 3(2): 147-52(2000)), vigor, development time (time to harvest), enhanced nutrient content, novel growth patterns, flavors or colors, salt, heat, drought, and cold tolerance (e.g., Sakamoto, et al., *J Exp Bot* 51(342):81-8 (2000); Saijo, et al., *Plant J* 23(3):319-327 (2000); Yeo, et al., *Mol Cells* 10(3):263-8 (2000); Cushman, et al., *Curr Opin Plant Bid* 3(2):117-24 (2000)), and the like. Those of skill will recognize that there are numerous polynucleotides from which to choose to confer these and other agronomically important traits.

In some embodiments, transgenic animals that express growth-enhancing payload polynucleotides (e.g., growth hormones) are created according to the methods of the invention. Prior to harvest of the animals, excision of the introduced transgenes can be induced, thus resulting in nontransgenic animals or animal parts. For example, transgenic animals, such as salmon, cattle, poultry, pigs, etc., expressing growth hormone payload genes are contemplated according to the methods of the invention.

Payload genes in cattle, for instance, include growth hormones such as bovine growth hormone or bovine somatotropin. See, e.g., Kopchick, et al., *Annu Rev Nutr* 19:437-61 (1999); Gordon, et al., *Mol Cell Endocrinol* November; 33(1):81-95 (1983). In another embodiment, the payload gene is the SKI gene (see, e.g., Bowen, et al., *Biol Reprod.* 50(3):664-8 (1994)). Payload genes in fish include the salmon growth hormone (Fletcher, et al. "Transgenic fish for aquaculture" In: Genetic Engineering (ed: J K. Setlow) Vol. 13: 331-370 (1991); and Hew, et al. *J. Fish. Biol.* (Supplement A) 47:1-19 (1995)).

Other payload genes include genes promoting disease resistance. Such genes include genes encoding antimicrobial products as well as antisense constructs to prevent expression of viral pathogens. For examples in fish, see, e.g., Zafloff, M., *Proc. Natl Acad. Sci. USA* 84:5449-53 (1997); and Grinde, B., *J. Fish Diseases* 12:95-104 (1989).

Similarly, transgenic pigs, poultry, or agriculturally important animals expressing growth hormones or genes to improve resistance to pathogens are contemplated by the invention.

In another embodiment, the invention provides for fish expressing increased levels of alpha hydroxy fatty acids. Such payload genes can be excised from the transgenic organism prior to sale of the fish to the public.

In some embodiments, the payload gene controls cholesterol biosynthesis. For example, cholesterol biosynthesis can be down regulated in mature chickens, thereby producing eggs with reduced cholesterol. For example, antisense constructs operably linked to a promoter expressed in adult chickens can be directed against transcripts encoding cholesterol biosynthetic enzymes, and introduced into chickens. Excision can then be induced or, alternatively, an egg-specific excision promoter can be used to then excise the transgenes in the egg, thereby producing a nontransgenic, low cholesterol egg.

Microorganism payload genes are also contemplated according to the methods of the invention. For example, alcoholic beverages are products of microbial fermentation and therefore can comprise polynucleotide constructs of the invention that improve the quality of the beverages. For instance in wine production, microorganisms (e.g., yeast) expressing enzymes for the degradation of tannins or other undesirable chemicals in wine can be used to improve the quality of wine. Excision of transgenes is then induced prior to sale of the beverage. Similarly, microorganisms expressing green fluorescent protein for colored beer production are contemplated. Excision of the transgene can then be induced prior to sale of the product.

In another aspect, yeast is modified to raise the content of tocopherol derived from In another embodiment, high nutrient (e.g., high protein) yoghurt is produced with transgenic microorganisms. Following production of the desired products, the transgenes are excised from the genomes of the microorganisms.

The invention also provides for microbial production of pharmaceuticals (e.g., subtilisin by *Bacillus subtilis*). In the industrial production of transgenic proteins, microbial effluents containing GMOs can be released into the environment. To avoid release of microbial waste effluent containing GMOs, the transgenes for pharmaceutical products can be excised from microorganisms of other cell cultures according to the methods of the invention.

IV. Methods of Preventing Excision of the Excision Construct

It is useful to have a system to maintain the excision construct of the invention in the organism, and importantly, in the reproductive organs under some conditions, for example, to propagate a new generation of GMOs. In general, a control polynucleotide can be introduced into the excision construct to achieve this goal. The control polynucleotide generally functions either to inhibit expression of the DNA sequence-specific DNA cleaving enzyme when inhibition is desired (e.g., when reproduction is desired) or to release repression of the excision promoter, thus allowing for expression from the excision promoter. As discussed above, the compositions and methods of the invention can be illustrated by reference to production of transgenic plants. One of skill in the art will recognize, however, that the same or similar embodiments can be applied to other organisms such as animals and microorganisms.

One application of the present invention is to produce transgenic plants that lack the transgene in seeds. Seed, fruit and other reproductive organs of plants are often the commercially valuable agricultural products of plants. For instance, the grains of monocots such as rice, wheat and corn are key food products. As described above, plants can be developed with a seed-specific promoter operably linked to a sequence-specific DNA cleaving enzyme that excises the construct in the seed. Without a method to prevent excision, however, it would be impossible to generate new transgenic plants aside from by vegetative propagation or other nonsexual methods. The present invention therefore provides for methods of maintaining a transgenic construct in a seed or other specific tissue as a further control of when and where the construct is excised in the plant. Those of skill will recognize that there are numerous variations for controlling or preventing expression of the sequence-specific DNA cleaving enzyme in a particular cell.

In one aspect, expression from the first excision promoter (i.e. the promoter operably linked to the first DNA cleaving enzyme, which excises the entire construct) can be countered by a second inducible promoter. For example, the second inducible promoter can be operably linked to a repressor gene, which, when expressed, prevents expression of the first excision promoter. Examples of repressors include the tet and lac repressors (Gatz, et al., *Mol. Gen. Genet.* 227:229-237 (1991). In some embodiments of this example, the first excision promoter is a fruit-specific plant promoter and the second inducible promoter is induced when transfer of the transgene to the fruit and seed is desired (e.g., for propagation of seed).

Alternatively, the second excision promoter can be linked to the polynucleotide encoding the first DNA cleaving enzyme in the opposite orientation of the first excision promoter (i.e., from the 3' end of the coding sequence towards the 5' end of the sequence), thereby interrupting expression of the DNA cleaving enzyme. In these embodiments, the transcriptional activity of the second promoter prevents completion of transcripts from the first excision promoter, thereby preventing expression of the sequence-specific DNA cleaving enzyme.

In other embodiments, an antisense polynucleotide can be operably linked to the second inducible promoter, thereby preventing the translation of the DNA cleaving enzyme mRNA. See, e.g., Sheehy et al., *Proc. Nat. Acad. Sci. USA*, 85:8805-8809 (1988), and Hiatt et al., U.S. Pat. No. 4,801, 340 for a description of antisense technology. In general, antisense technology involves the generation of RNA transcripts that hybridize to a target transcript (i.e., the transcript encoding the sequence-specific DNA cleaving enzyme). Alternatively, the second inducible promoter can be operably linked to a DNA cleaving enzyme polynucleotide in the sense orientation to induce sense suppression of the gene. See, e.g., Napoli et al., *The Plant Cell* 2:279-289 (1990), and U.S. Pat. Nos. 5,034,323, 5,231,020, and 5,283,184 for a description of sense suppression technology.

In some embodiments, aptamer technology can be used to repress expression of the first excision promoter. See, e.g., Hermann, et al., *Science* 287(5454):820-5 (2000); and Famulok, et al., *Curr Top Microbiol Immunol* 243:123-36 (1999). For example, a small oligonucleotide could be developed that only binds and represses the first excision promoter when stabilized by a particular chemical which can be applied when transgenic seed are desired. For example, combinatorial library selections through the systematic evolution of ligands by exponential enrichment (SELEX) technique can be used to identify nucleic acid aptamers that bind with high-affinity and specificity to a wide range of selected molecules. See, e.g., Conrad, et al, *Mol Divers* 1(1):69-78 (1995); and Kusser, *J Biotechnol* 74(1):27-38 (2000).

In some embodiments, the first excision promoter is induced by low moisture. In this embodiment, the promoter would drive expression of the DNA cleaving enzyme in the grain (dry), thereby excising the transgenic construct, but would not function in the seed (moist), thereby allowing for propagation of the transgenic plants.

Figure 2:
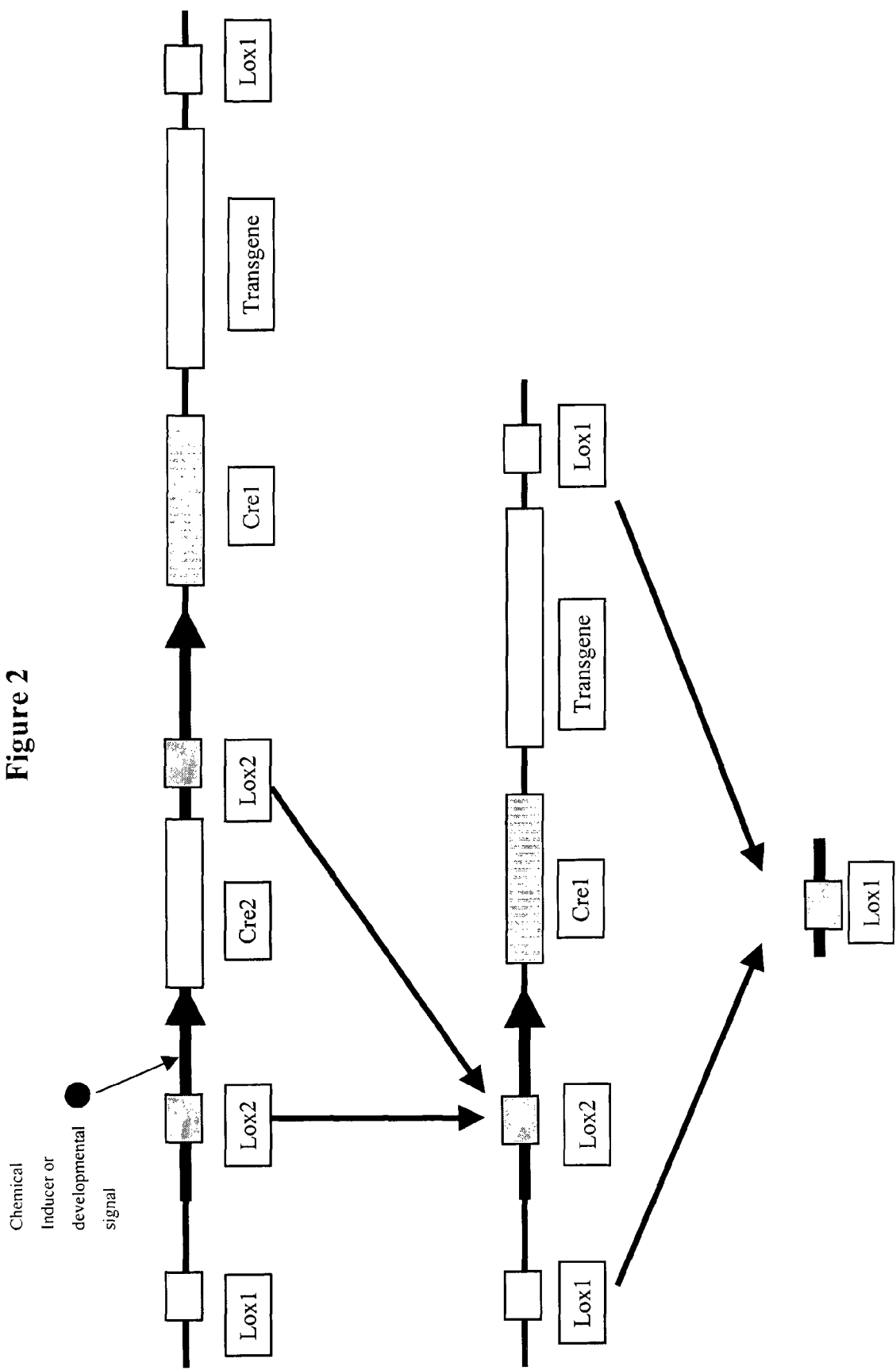
FIG. 2 is a schematic representation of a multi-tiered system for maintenance of a polynucleotide construct and illustrates a method for priming the system to excise the construct under specific conditions. Horizontal arrows indicate promoters.

In some embodiments, a multi-tiered excision system is used. For example, the first excision promoter can be interrupted by a second pair of recognition sequences flanking a chemically-induced promoter operably linked to a polynucleotide encoding a second sequence-specific DNA cleaving enzyme (FIG. 2). In general, this system allows for the transgenic construct to remain intact in the genome and be propagated to the next generation so long as the chemical inducer is not provided. Once the chemical inducer is presented, the second DNA cleaving enzyme is induced and excises its own coding region and flanking recognition sequences, thereby leaving the first excision promoter intact. Assuming the first excision promoter is a seed-specific promoter, for instance, the promoter will then become active in seed in plants treated with the inducer (FIG. 2). Resulting seed will subsequently be non-transgenic and subsequent progeny will be non-transgenic.

V. Target Organisms

The methods of the invention are useful for obtaining non-transgenic tissues or cells from organisms that are transgenic (termed partially transgenic organisms). The methods of the invention can be applied to cells of any organisms, including cells from animals, plants, fungi, bacteria and other microorganisms. In some embodiments, the cells are part of a multicellular organism, i.e., a transgenic plant or animal. However, unicellular microorganisms that are transgenic for only part of their life cycle can also be developed according to the methods of the invention.

Exemplary organisms include agricultural plant crops, e.g., grain, fruit and vegetable crop plants. The invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna*, and *Zea*.

Other exemplary organisms include agricultural animals such as cattle, pigs and poultry, as well as fish, including salmon. Microorganisms include yeast (*Sacromyces cervisae*) and bacteria (e.g., *Bacillus* sp., *Streptococcus thermophilus* and *Lactobacillus* sp. such as *L. bulgaricus* and *L. acidophilus*).

VI. Construction of the Polynucleotide Constructs of the Invention

Typically, constructs to be introduced into these cells are prepared using transgene expression techniques. Recombinant expression techniques involve the construction of recombinant nucleic acids and the expression of genes in transfected cells. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology*, Volume 152, Academic Press, Inc., San Diego, Calif. (Berger); and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel).

Generally, a gene to be expressed will be present in an expression cassette, meaning that the gene is operably linked to expression control signals, e.g., promoters and terminators, that are functional in the host cell of interest. The genes that encode the sequence-specific DNA cleaving enzyme and, optionally, the selectable marker, will also be under the control of such signals that are functional in the host cell. Control of expression is most easily achieved by selection of a promoter. The transcription terminator is not generally as critical and a variety of known elements may be used so long as they are recognized by the cell. The invention contemplates polynucleotides operably linked to a promoter in the sense or antisense orientation.

The construction of polynucleotide constructs generally requires the use of vectors able to replicate in bacteria. A plethora of kits are commercially available for the purification of plasmids from bacteria. For their proper use, follow the manufacturer's instructions (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, used to transfect cells or incorporated into *Agrobacterium tumefaciens* to infect and transform plants. Where *Agrobacterium* is the means of transformation, shuttle vectors are constructed. Cloning in *Streptomyces* or *Bacillus* is also possible.

Selectable markers are often incorporated into the polynucleotide constructs and/or into the vectors that are used to introduce the constructs into the target cells. These markers permit the selection of colonies of cells containing the polynucleotide of interest. Often, the vector will have one selectable marker that is functional in, e.g., *E. coli*, or other cells in which the vector is replicated prior to being introduced into the target cell. Examples of selectable markers for *E. coli* include: genes specifying resistance to antibiotics, i.e., ampicillin, tetracycline, kanamycin, erythromycin, or genes conferring other types of selectable enzymatic activities such as β-galactosidase, or the lactose operon. Suitable selectable markers for use in mammalian cells include, for example, the dihydrofolate reductase gene (DHFR), the thymidine kinase gene (TK), or prokaryotic genes conferring drug resistance, gpt (xanthine-guanine phosphoribosyltransferase, which can be selected for with mycophenolic acid; neo (neomycin phosphotransferase), which can be selected for with G418, hygromycin, or puromycin; and DHFR (dihydrofolate reductase), which can be selected for with methotrexate (Mulligan & Berg (1981) *Proc. Nat'l. Acad. Sci. USA* 78: 2072; Southern & Berg (1982) *J. Mol. Appl. Genet.* 1: 327).

Selection markers for plant cells often confer resistance to a biocide or an antibiotic, such as, for example, kanamycin, G 418, bleomycin, hygromycin, or chloramphenicol, or herbicide resistance, such as resistance to chlorsulfuron or Basta. Examples of suitable coding sequences for selectable markers are: the neo gene which codes for the enzyme neomycin phosphotransferase which confers resistance to the antibiotic kanamycin (Beck et al (1982) *Gene* 19:327); the hyg gene, which codes for the enzyme hygromycin phosphotransferase and confers resistance to the antibiotic hygromycin (Gritz and Davies (1983) *Gene* 25:179); and the bar gene (EP 242236) that codes for phosphinothricin acetyl transferase which confers resistance to the herbicidal compounds phosphinothricin and bialaphos.

VII. Methods for Introducing Constructs into Target Cells

The polynucleotide constructs having flanking recombination sites can be introduced into the target cells and/or organisms by any of the several means known to those of skill in the art. For instance, the DNA constructs can be introduced into cells, either in culture or in the organs of a plant by a variety of conventional techniques. For example, the DNA constructs can be introduced directly to plant cells using ballistic methods, such as DNA particle bombardment, or the DNA construct can be introduced using techniques such as electroporation and microinjection of cell. Particle-mediated transformation techniques (also known as "biolistics") are described in, e.g., Klein et al., *Nature*, 327:70-73 (1987); Vasil, V. et al., *Bio/Technol.* 11:1553-1558 (1993); and Becker, D. et al., *Plant J.*, 5:299-307 (1994). These methods involve penetration of cells by small particles with the nucleic acid either within the matrix of small beads or particles, or on the surface. The biolistic PDS-1000 Gene Gun (Biorad, Hercules, Calif.) uses helium pressure to accelerate DNA-coated gold or tungsten microcarriers toward target cells. The process is applicable to a wide range of tissues and cells from organisms, including plants, bacteria, fungi, algae, intact animal tissues, tissue culture cells, and animal embryos. One can employ electronic pulse delivery, which is essentially a mild electroporation format for live tissues in animals and patients. Zhao, *Advanced Drug Delivery Reviews* 17:257-262 (1995).

Other transformation methods are also known to those of skill in the art. Microinjection techniques are known in the art and well described in the scientific and patent literature. The introduction of DNA constructs using polyethylene glycol (PEG) precipitation is described in Paszkowski et al., *EMBO J.* 3:2717 (1984). Electroporation techniques are described in Fromm et al., *Proc. Natl. Acad. Sci. USA*, 82:5824 (1985). PEG-mediated transformation and electroporation of plant protoplasts are also discussed in Lazzeri, P., *Methods Mol. Biol.* 49:95-106 (1995). Methods are known for introduction and expression of heterologous genes in both monocot and dicot plants. See, e.g., U.S. Pat. Nos. 5,633,446, 5,317,096, 5,689,052, 5,159,135, and 5,679,558; Weising et al. (1988) *Ann. Rev. Genet.* 22:421-477. Transformation of monocots in particular can use various techniques including electroporation (e.g., Shimamoto et al., *Nature* (1992), 338:274-276; biolistics (e.g., European Patent Application 270,356); and *Agrobacterium* (e.g., Dytebier et al., *Proc. Nat'l Acad. Sci. USA* (1987) 84:5345-5349).

For transformation of plants, DNA constructs may be combined with suitable T-DNA flanking regions and introduced into a conventional *Agrobacterium tumefaciens* host vector. The virulence functions of the *A. tumefaciens* host will direct the insertion of a transgene and adjacent marker gene(s) (if present) into the plant cell DNA when the cell is infected by the bacteria. *Agrobacterium tumefaciens*-mediated transformation techniques are well described in the scientific literature. See, for example, Horsch et al. *Science*, 233:496-498 (1984), Fraley et al., *Proc. Natl. Acad. Sci. USA*, 80:4803 (1983), and Hooykaas, *Plant Mol. Biol.*, 13:327-336 (1989), Bechtold et al., *Comptes Rendus De L Academie Des Sciences Serie Iii-Sciences De La Vie-Life Sciences*, 316:1194-1199 (1993), Valvekens et al.,*Proc. Natl. Acad. Sci. USA*, 85:5536-5540 (1988). For a review of gene transfer methods for plant and cell cultures, see, Fisk et al., *Scientia Horticulturae* 55:5-36 (1993) and Potrykus, *CIBA Found. Symp.* 154:198 (1990).

Other methods for delivery of polynucleotide sequences into cells include, for example liposome-based gene delivery (Debs and Zhu (1993) WO 93/24640; Mannino and Gould-Fogerite (1988) *BioTechniques* 6(7): 682-691; Rose U.S. Pat. No. 5,279,833; Brigham (1991) WO 91/06309; and Felgner et al. (1987) *Proc. Natl. Acad. Sci. USA* 84: 7413-7414), as well as use of viral vectors (e.g., adenoviral (see, e.g., Berns et al. (1995) *Ann. NY Acad. Sci.* 772: 95-104; Ali et al. (1994) *Gene Ther.* 1: 367-384; and Haddada et al. (1995) *Curr. Top. Microbiol. Immunol.* 199 (Pt 3): 297-306 for review), papillomaviral, retroviral (see, e.g., Buchscher et al. (1992) *J. Virol.* 66(5) 2731-2739; Johann et al. (1992) *J. Virol.* 66 (5):1635-1640 (1992); Sommerfelt et al., (1990) *Virol.* 176: 58-59; Wilson et al. (1989) *J. Virol.* 63:2374-2378; Miller et al., *J. Virol.* 65:2220-2224 (1991); Wong-Staal et al., PCT/US94/05700, and Rosenburg and Fauci (1993) in *Fundamental Immunology, Third Edition* Paul (ed) Raven Press, Ltd., New York and the references therein, and Yu et al., *Gene Therapy* (1994) supra.), and adeno-associated viral vectors (see, West et al. (1987) *Virology* 160:38-47; Carter et al. (1989) U.S. Pat. No. 4,797,368; Carter et al. WO 93/24641 (1993); Kotin (1994) *Human Gene Therapy* 5:793-801; Muzyczka (1994) *J. Clin. Invst.* 94:1351 and Samulski (supra) for an overview of AAV vectors; see also, Lebkowski, U.S. Pat. No. 5,173,414; Tratschin et al. (1985) *Mol. Cell. Biol.* 5(11):3251-3260; Tratschin et al (1984) *Mol. Cell. Biol.*, 4:2072-2081; Hermonat and Muzyczka (1984) *Proc. Natl. Acad. Sci. USA*, 81:6466-6470; McLaughlin et al. (1988) and Samulski et al. (1989) *J. Virol.*, 63:03822-3828), and the like.

VIII. Regeneration of Transgenic Plants and Animals

The methods of the invention are particularly useful for obtaining transgenic and chimeric multicellular organisms that have at least one copy of a desired exogenous polynucleotide. Methods for obtaining transgenic and chimeric organisms, both plants and animals, are well known to those of skill in the art.

Transformed plant cells, derived by any of the above transformation techniques, can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, Macmillian Publishing Company, New York (1983); and in Binding, *Regeneration of Plants, Plant Protoplasts*, pp. 21-73, CRC Press, Boca Raton, (1985). Regeneration can also be obtained from plant callus, explants, somatic embryos (Dandekar et al., *J. Tissue Cult. Meth.*, 12:145 (1989); McGranahan et al., *Plant Cell Rep.*, 8:512 (1990)), organs, or parts thereof. Such regeneration techniques are described generally in Klee et al., *Ann. Rev. of Plant Phys.*, 38:467-486 (1987).

The nucleic acids of the invention can be used to confer desired traits on essentially any plant. One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The methods are useful for producing transgenic and chimeric animals of most vertebrate species. Such species include, but are not limited to, nonhuman mammals, including rodents such as mice and rats, rabbits, ovines such as sheep and goats, porcines such as pigs, and bovines such as cattle and buffalo. Methods of obtaining transgenic animals are described in, for example, Puhler, A., Ed., *Genetic Engineering of Animals*, VCH Publ., 1993; Murphy and Carter, Eds., *Transgenesis Techniques: Principles and Protocols* (*Methods in Molecular Biology*, Vol. 18), 1993; and Pinkert, C A, Ed., *Transgenic Animal Technology: A Laboratory Handbook*, Academic Press, 1994. Transgenic fish having specific genetic modifications can also be made using the claimed methods. See, e.g., Iyengar et al. (1996) *Transgenic Res.* 5: 147-166 for general methods of making transgenic fish.

One method of obtaining a transgenic or chimeric animal having specific modifications in its genome is to contact fertilized oocytes with a vector that includes the polynucleotide of interest flanked by recombination sites. For some animals, such as mice, fertilization is performed in vivo and fertilized ova are surgically removed. In other animals, particularly bovines, it is preferably to remove ova from live or slaughterhouse animals and fertilize the ova in vitro. See DeBoer et al., WO 91/08216. In vitro fertilization permits the modifications to be introduced into substantially synchronous cells. Fertilized oocytes are then cultured in vitro until a pre-implantation embryo is obtained containing about 16-150 cells. The 16-32 cell stage of an embryo is described as a morula. Pre-implantation embryos containing more than 32 cells are termed blastocysts. These embryos show the development of a blastocoel cavity, typically at the 64 cell stage. If desired, the presence of a desired exogenous polynucleotide in the embryo cells can be detected by methods known to those of skill in the art. Methods for culturing fertilized oocytes to the pre-implantation stage are described by Gordon et al. (1984) *Methods Enzymol.* 101: 414; Hogan et al. *Manipulation of the Mouse Embryo: A Laboratory Manual*, C.S.H.L. N.Y. (1986) (mouse embryo); Hammer et al. (1985) *Nature* 315: 680 (rabbit and porcine embryos); Gandolfi et al. (1987) *J. Reprod. Fert.* 81: 23-28; Rexroad et al. (1988) *J. Anim. Sci.* 66: 947-953 (ovine embryos) and Eyestone et al. (1989) *J. Reprod. Fert.* 85: 715-720; Camous et al. (1984) *J. Reprod. Fert.* 72: 779-785; and Heyman et al. (1987) *Theriogenology* 27: 5968 (bovine embryos). Sometimes pre-implantation embryos are stored frozen for a period pending implantation. Pre-implantation embryos are transferred to an appropriate female resulting in the birth of a transgenic or chimeric animal depending upon the stage of development when the transgene is integrated. Chimeric mammals can be bred to form true germline transgenic animals.

Alternatively, the methods can be used to obtain embryonic stem cells (ES) that have a single copy of the desired exogenous polynucleotide. These cells are obtained from preimplantation embryos cultured in vitro. See, e.g., Hooper, M L, *Embryonal Stem Cells: Introducing Planned Changes into the Animal Germline* (Modern Genetics, v. 1), Int'l. Pub. Distrib., Inc., 1993; Bradley et al. (1984) *Nature* 309, 255-258. Transformed ES cells are combined with blastocysts from a non-human animal. The ES cells colonize the embryo and in some embryos form the germ line of the resulting chimeric animal. See Jaenisch, *Science,* 240: 1468-1474 (1988). Alternatively, ES cells or somatic cells that can reconstitute an organism ("somatic repopulating cells") can be used as a source of nuclei for transplantation into an enucleated fertilized oocyte giving rise to a transgenic mammal. See, e.g., Wilmut et al. (1997) *Nature* 385: 810-813.

EXAMPLES

The following example is offered to illustrate, but not to limit the present invention.

Example 1

Example 1

This example demonstrates chemical induction and tissue-specific induction of transgenes in plants.

Construction of Vectors

A shuttle vector plasmid containing an "excision" cassette flanked by loxP sites (Rossant, J. and Nagy, A., *Nature Med.* 1:592-594 (1995)) within a T-DNA transformation cassette is constructed. Construction of the shuttle vector is performed using standard recombinant DNA manipulation techniques. The excision cassette comprises two gene expression cassettes. First, the excision cassette contains a T-DNA comprising a *Bacillus thuringiensis* insecticidal protein gene operably linked to a constitutive promoter. Second, the excision cassette contains the Cre gene operably linked to an "excision" promoter. The excision cassette is flanked by loxP sites.

Two different Cre expression cassettes are constructed. In the first Cre expression cassette, the "excision" promoter is an alcohol-inducible promoter, which does not initiate transcription in the presence of the AlcR negative regulator. To supply the AlcR gene product, a CaMV 35S promoter is operably linked to the AlcR gene. The AlcR gene product acts as a negative regulator that inhibits transcription from the AlcA promoter in the absence of ethanol.

In the second Cre expression cassette, the promoter is the seed-specific promoter from the napA gene of *Brassica napus* (GenBank No. J02798, Josefsson et al. *JBL* 26:12196-1301 (1987).

Following their construction, the first excision cassette and the second excision cassettes are introduced into separate T-DNA cassettes in a plasmid vector capable of replication in *Agrobacterium*.

Transformation of Plants

The T-DNA constructs are then introduced into *Brassica napus* plants using standard *Agrobacterium*-based transformation and regeneration techniques (Thomzik, *Methods Mol Biol* 44:79-85 (1995)). After transgenic plants are recovered, plants with single-copy, homozygous T-DNA insertions are obtained by standard genetic and molecular techniques.

Chemical Induction of Transgene Deletion

For those plants containing the AlcA/AlcR regulon, the AlcA promoter is induced by applying a 5% ethanol solution to the root system of the transgenic plants. In separate plants, the aerial parts of the plant are exposed to ethanol vapors by enclosing the plant in a sealed container including a pot of ethanol to act as a source of ethanol vapor for 24 hours. The quantity of ethanol vapor can be measured using a gas-tight syringe to extract some vapor and measure the quantity of ethanol with gas chromatography.

Induction of the promoter and subsequent excision of the excision cassette is measured by standard hybridization techniques. A probe specific for the excision cassette is hybridized from DNA sampled from treated and untreated plants. Plants treated with ethanol do not contain DNA that hybridizes with the probe, whereas DNA from transformed, but untreated plants, does hybridize. As a control, a probe specific for DNA that is not excised hybridizes to all DNA samples.

Tissue-specific Induction of Transgene Deletion

A similar approach is used to detect excision from plants expressing Cre from the napA seed-specific promoter. In this case, seed tissue and non-seed tissue (e.g., leaf tissue) is collected from the plants and DNA is extracted. Probes specific for the excision cassette are tested for hybridization to both DNA samples. The probes hybridize to the DNA from leaf tissue, but does not hybridize to DNA extracted from seed, indicating that the excision cassette has excised in the seed.

Example 2

This example demonstrates the induction of excision of transgenes in microbial hosts.

Plasmid Construction in *E. coli*

A plasmid comprising an "excision" cassette containing the β-galactosidase gene operably linked to a constitutive promoter and the Cre recombinase gene operably linked to the lacZ promoter is constructed. The excision cassette is flanked by loxP sequences. *E. coli* is then transfected with the resulting plasmid.

The resulting *E. coli* strain is then grown in minimal media broth under constant shaking at 37° C. until the culture is moderately turbid. One aliquot of bacteria is then plated on agar media comprising X-gal. Blue colonies of bacteria form, demonstrating that the strain is constitutively expressing β-galactosidase Excision of the excision cassette from the *E. coli* strain is then induced. First, an aliquot of the moderately turbid bacterial broth is added to a new flask of minimal media to induce new bacterial growth. The new flask contains 10 mM IPTG, i.e., a concentration sufficient to induce the lacZ promoter. After the bacteria have grown in the presence of IPTG (approximately 18 hours), an aliquot of the broth is plated on agar media comprising X-gal. The bacteria are plated in a concentration to form single colonies. The ratio of white to blue colonies that subsequently develop on the plates provides a measure of the excision efficiency, thereby demonstrating the induction of an excision event in a microbial host.

It is understood that the example and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of creating a transgenic maize plant capable of producing a non-transgenic agricultural product, the method comprising,
    introducing into a maize plant a polynucleotide excision construct flanked by a first pair of recognition sequences, the construct comprising,
        a first expression cassette comprising a first excision promoter operably linked to a polynucleotide encoding a first sequence-specific DNA cleaving enzyme, wherein the first excision promoter is not constitutive; and
        a second expression cassette comprising a promoter operably linked to a payload polynucleotide conferring an agronomically important trait on the maize plant; wherein expression of said payload polynucleotide produces a phenotype in said maize plant that is useful or advantageous for food production or food products, and said agronomically important trait is not a hormone biosynthesis gene leading to the production of a plant hormone; and
    expressing the first sequence-specific DNA cleaving enzyme, thereby cleaving the recognition sequences and excising the excision construct from at least part of the transgenic maize plant and thereby producing a non-transgenic agricultural product in the part of the maize plant wherein said excision occurs.

2. The method of claim 1, wherein the polynucleotide excision construct is excised from the entire transgenic maize plant.

3. The method of claim 1, wherein the first excision promoter is inducible.

4. The method of claim 3, wherein the first excision promoter is chemically inducible.

5. The method of claim 1, wherein the first excision promoter is induced under low moisture conditions.

6. The method of claim 1, wherein the first sequence-specific DNA cleaving enzyme cleaves within the recognition sequence.

7. The method of claim 6, wherein the first sequence-specific DNA cleaving enzyme is selected from the group comprising recombinases, resolvases, restriction enzymes and transposases.

8. The method of claim 7, wherein the sequence-specific DNA cleaving enzyme is a recombinase.

9. The method of claim 8, wherein the recombinase is Cre and the recognition sequence is a lox sequence.

10. An isolated nucleic acid comprising a polynucleotide excision construct flanked by a first pair of recognition sequences, the construct comprising,
    a first expression cassette comprising a first excision promoter operably linked to a polynucleotide encoding a first sequence-specific DNA cleaving enzyme, wherein the first excision promoter is not constitutive; and
    a second expression cassette comprising a promoter operably linked to a payload polynucleotide conferring an agronomically important trait on a maize plant, wherein expression of said payload polynucleotide produces a phenotype in said maize plant that is useful or advantageous for food production or food products, and said agronomically important trait is not a hormone biosynthesis gene leading to the production of a plant hormone, wherein expression of said first sequence-specific DNA cleavage enzyme in the maize plant excises the excision construct from at least part of the maize plant and thereby produces a non-transgenic agricultural product in the part of the maize plant wherein excision occurs.

11. The nucleic acid of claim 10, wherein the first excision promoter is inducible.

12. The nucleic acid of claim 10, wherein the first excision promoter is induced under low moisture conditions.

13. The nucleic acid of claim 10, wherein the first sequence-specific DNA cleaving enzyme cleaves within the recognition sequence.

14. The nucleic acid of claim 13, wherein the first sequence-specific DNA cleaving enzyme is selected from the group comprising recombinases, resolvases, restriction enzymes and transposases.

15. The nucleic acid of claim 14, wherein the sequence-specific DNA cleaving enzyme is a recombinase.

16. The nucleic acid of claim 15, wherein the recombinase is Cre and the recognition sequence is a lox sequence.

17. A maize plant comprising a polynucleotide excision construct flanked by two recognition sequences, the construct comprising,
    a first expression cassette comprising a first excision promoter operably linked to a polynucleotide encoding a sequence-specific DNA cleaving enzyme, wherein the first excision promoter is not constitutive; and
    a second expression cassette comprising a promoter operably linked to a payload polynucleotide conferring an agronomically important trait on a maize plant, wherein expression of said payload polynucleotide produces a phenotype in said maize plant that is useful or advantageous for food production or food products, and said agronomically important trait is not a hormone biosynthesis gene leading to the production of a plant hormone, wherein expression of said sequence-specific DNA cleavage enzyme excises the excision construct from at least part of the maize plant and thereby produces a non-transgenic agricultural product in the part of the maize plant wherein said excision occurs and the first excision promoter is induced under low moisture conditions.

18. The maize plant of claim 17, wherein the first sequence-specific DNA cleaving enzyme cleaves within the recognition sequence.

19. The maize plant of claim 18, wherein the first sequence-specific DNA cleaving enzyme is selected from the group comprising recombinases, resolvases, restriction enzymes and transposases.

20. The maize plant of claim 19, wherein the first sequence-specific DNA cleaving enzyme is a recombinase.

21. The maize plant of claim 20, wherein the recombinase is Cre and the recognition sequence is a lox sequence.

22. The maize plant of claim 17, wherein at least one cell of the maize plant is free of the excision construct.

23. The method of claim 8, wherein said recombinase comprises FLP and the first pair of recognition sequences comprise FRT sites.

24. The method of claim 1, wherein said maize plant is a grain crop maize plant.

25. The method of claim 24, wherein said grain crop maize plant is from the genera *Zea*.

26. The isolated nucleic acid of claim 15, wherein said recombinase comprises FLP and the first pair of recognition sequences comprise FRT sites.

27. The nucleic acid of claim 10, wherein said maize plant is a grain crop maize plant.

28. The nucleic acid of claim 27, wherein said grain crop maize plant is from the genera *Zea*.

29. The maize plant of claim 20, wherein said recombinase comprises FLP and the first pair of recognition sequences comprise FRT sites.

30. The maize plant of claim 17, wherein said maize plant is a grain crop maize plant.

31. The maize plant of claim 30, wherein said grain crop maize plant is from the genera Zea.

* * * * *

UNITED STATES PATENT AND TRADEMARK OFFICE
CERTIFICATE OF CORRECTION

PATENT NO. : 7,560,622 B2
APPLICATION NO. : 09/970004
DATED : July 14, 2009
INVENTOR(S) : Stemmer Page 1 of 1

It is certified that error appears in the above-identified patent and that said Letters Patent is hereby corrected as shown below:

<u>Title page,</u>
Item (57) ABSTRACT,
Line 3, "trausgenic" should read --transgenic--.

<u>Column 10,</u>
Line 21, "MOLECULE" should read --MOLECULAR--.

<u>Column 12,</u>
Line 16, "*Bid*" should read --*Biol*--.

<u>Column 17,</u>
Line 27, "Dytebier" should read --Bytebier--;
Line 50, "Felgner" should read --Feigner--.

Signed and Sealed this

Twenty-second Day of December, 2009

David J. Kappos
*Director of the United States Patent and Trademark Office*